US012702740B2

(12) United States Patent
Hiligh

(10) Patent No.: US 12,702,740 B2
(45) Date of Patent: Aug. 11, 2026

(54) TREATMENT OF BLEEDING WOUNDS

(71) Applicant: Wilbur Hiligh, Fort Washington, MD (US)

(72) Inventor: Wilbur Hiligh, Fort Washington, MD (US)

( * ) Notice: Subject to any disclaimer, the term of this patent is extended or adjusted under 35 U.S.C. 154(b) by 1082 days.

(21) Appl. No.: 17/826,347

(22) Filed: May 27, 2022

(65) Prior Publication Data

US 2023/0381394 A1 Nov. 30, 2023

(51) Int. Cl.

*A61M 1/36* (2006.01)
*A61M 1/04* (2006.01)

(52) U.S. Cl.

CPC .......... *A61M 1/36225* (2022.05); *A61M 1/04* (2013.01); *A61M 1/36223* (2022.05); *A61M 1/362264* (2022.05); *A61M 1/3627* (2013.01); *A61M 2205/3334* (2013.01); *A61M 2205/3344* (2013.01); *A61M 2205/3368* (2013.01); *A61M 2230/30* (2013.01)

(58) Field of Classification Search

CPC ................ A61M 1/36225; A61M 1/04; A61M 1/36223; A61M 1/362264; A61M 1/3627; A61M 2205/3334; A61M 2205/3344; A61M 2205/3368; A61M 2230/30; A61M 1/34; A61M 1/3623; A61M 1/90; A61M 1/96; A61M 1/98; A61M 1/36; A61M 1/3621; A61M 1/3633; A61M 1/3639; A61M 1/3672; A61M 1/3673; A61M 1/369

See application file for complete search history.

(56) References Cited

U.S. PATENT DOCUMENTS

| | | | | |
|---|---|---|---|---|
| 5,876,611 | A * | 3/1999 | Shettigar | A61M 1/3692 210/650 |
| 2009/0320684 | A1 * | 12/2009 | Weaver | A61M 1/1668 96/12 |
| 2016/0346452 | A1 * | 12/2016 | Gilbert | A61M 1/369 |
| 2022/0095940 | A1 * | 3/2022 | Banet | A61B 5/02141 |
| 2022/0249756 | A1 * | 8/2022 | Chawla | A61M 1/3616 |

* cited by examiner

*Primary Examiner* — Jason E Flick
(74) *Attorney, Agent, or Firm* — Robert Goozner

(57) ABSTRACT

An apparatus for treating a hemorrhaging wound and returning blood to the body includes at least one vacuum hose; tubing to return blood to the body; a reservoir to temporarily contain the blood, an ejectable filter between the vacuum hose and the reservoir, a temperature regulator to regulate the temperature in the reservoir; at least one pressure regulator connected to the at least one vacuum hose; a vacuum pump connected to the at least one pressure regulator, and an infusion pump connected to the tubing to return blood to the body. Blood is returned to the body via multi access catheter and/or consistent with present and future rapid infusion procedural methods that could change according to severity of injuries and the need for alternate vascular access points and/or infusion delivery protocols.

19 Claims, 14 Drawing Sheets

Vessel Closed to Atmosphere
218
216
220
222c
222d
222e
222a
204
206
202
222b
208
214
212
210

Vessel Open to Atmosphere
302
304
306
308
310
312
314
316
318
320
322
324

400
402
402a
404
404a
406
406a
406b
408
410
412
414
416
418
424
Transparent Plastic Reservoir Unit 520
514
Hydrophobic Vacuum Attachment
504
502
520
518
522
504
516
508
506
504
512
518
510

FIG. 6

Adhesive Vacuum Attachment

602
Side View
604
606
608
610

604
606
Top View 612

FIG. 8A

REAR OF UNIT WITH FILTER EJECTION

TREATMENT OF BLEEDING WOUNDS

FIELD OF DISCLOSURE

The present disclosure relates generally to a method and apparatus to treat bleeding wounds and to return blood to the body.

BACKGROUND

Bleeding wounds are typically treated by placing a sterile bandage or a clean cloth on the wound and applying constant pressure until the bleeding stops. However in severe wounds there is frequently a severe hemorrhaging of blood. Hypovolemic shock occurs when the body begins to shut down due to the loss of large amounts of blood or fluid. When hypovolemic shock is caused by blood loss, it's known as hemorrhagic shock. People with injuries that involve heavy bleeding may go into hemorrhagic shock if the bleeding isn't stopped immediately.

Common causes of hemorrhagic shock include sever, burns, deep cuts, gunshot wounds, trauma and amputations. Blood carries oxygen and other essential substances to your organs and tissues. When heavy bleeding occurs, these substances are lost more quickly than they can be replaced. There's not enough blood flow to the organs in the body, and they begin to shut down. As the heart shuts down and fails to circulate an adequate amount of blood through the body, symptoms of shock occur. Blood pressure plummets and there's a massive drop in body temperature, which can be life threatening.

Signs of hemorrhagic shock include blue lips and fingernails, low or no urine output, excessive sweating, shallow breathing, dizziness or loss of consciousness, confusion, chest pain, low blood pressure, rapid heart rate, weak pulse and anxiety and a sense of impending doom.

Hemorrhagic shock is frequently treated by Emergency Medical Technicians (EMT) at the site of the accident or occurrence. However, there is a limited amount of blood or plasma in the ambulance at the scene. As a result, there is a serious possibility that a severely wounded patient may die or suffer irreversible damage before arriving at the hospital.

One approach is to use hydroxyethyl-starch (HES) solutions to treat hypovolemia (low blood volume) caused by acute (sudden) blood loss. However, the doctor or nurse should monitor the patient's kidney function after HES administration. Also, both natural and synthetic colloids contain large molecules that cannot cross an intact vascular barrier. This confers the appealing theoretical benefit of a volume-sparing effect with a decreased risk of inducing a positive fluid balance with secondary adverse effects (such as heart failure, pulmonary edema, peripheral edema). Despite their initial promise, multiple adverse effects as well as lack of a survival benefit have recently caused colloid therapy to fall out of favor in human medicine. Significant debate surrounds the safety of HES solutions with the most recent clinical data prompting the ban of their use in Europe and guidelines recommending against their use in certain patient populations.

Moreover, there has been a significant drop in donations during the Covid-19 pandemic, and weather conditions and staffing limitations have caused ongoing cancelation of planned blood drives. There's been a 10% overall blood donation decline since March 2020, and a 62% drop in college and high school blood drives during the pandemic.

As a result, there is a need to recycle blood and to address severe hemorrhaging in situ by the EMT.

The Background section of this document is provided to place embodiments of the present disclosure in technological and operational context, to assist those of skill in the art in understanding their scope and utility. Unless explicitly identified as such, no statement herein is admitted to be prior art merely by its inclusion in the Background section.

SUMMARY

The following presents a simplified summary of the disclosure in order to provide a basic understanding to those of skill in the art. This summary is not an extensive overview of the disclosure and is not intended to identify key/critical elements of embodiments of the disclosure or to delineate the scope of the disclosure. The sole purpose of this summary is to present some concepts disclosed herein in a simplified form as a prelude to the more detailed description that is presented later.

Briefly described, an embodiment of the disclosure relates to suctioning blood from a hemorrhaging wound, briefly, storing the blood and returning the blood to the patient via at least one infusion catheter.

In one embodiment, the disclosure pertains to an apparatus to treat a hemorrhaging wound, which includes at least one vacuum hose, at least one tubing to return blood to the body, a reservoir to temporarily contain the blood, an ejectable filter between the vacuum hose and the reservoir, a temperature regulator to regulate the temperature in the reservoir, at least one pressure regulator connected to the at least one vacuum hose, at least one vacuum pump connected to the at least one pressure regulator, and at least one infusion pump connected to the tubing to return blood to the body.

In another embodiment, there are at least 2 vacuum hoses and a vacuum pump switch connected to each vacuum hose. An infusion pump switch may be connected to each infusion pump.

In another embodiment, there are 3 infusion tubings, catheters or multi access catheters to return blood to the body, with each tubing being attached to a separate infusion pump. Also, the reservoir may be a transparent plastic reservoir. A first replaceable, ejectable filter may be downstream from each vacuum pump, a second replaceable filter downstream from each infusion pump, and a separate tubing or catheter to return blood to the body. Each replaceable filter may be an about 20 to about 300 micron pore size heated aluminum/steel mesh filter, with a typical filter having an about 200 micron pore size.

In the disclosure, a blood pressure cuff may be in electronic contact with the apparatus, and the apparatus includes a blood pressure display in communication with the blood pressure cuff.

In another embodiment, the apparatus is attached to a hydrophobic vacuum attachment for treating a chest wound, the hydrophobic vacuum attachment formed from a pillow part attached to a drain part having a vacuum connection point and an air vent. Alternately, an adhesive vacuum attachment includes a suction head, an adhesive layer on the suction head, a vacuum connection port on the suction head, and an air vent in communication with the vacuum connection port.

In an embodiment, the disclosure pertains to a procedure for treating a hemorrhaging wound, which includes providing the apparatus, administering a dose of anticoagulant to the apparatus before or during the procedure, applying a vacuum to vacuum blood from the hemorrhaging wound, applying a vacuum to vacuum blood from the hemorrhaging wound, turning on the at least one infusion pump, filling iv tubing to a tip of the insertion attachment, expelling a small quantity of blood to clear the iv tubing of any trapped air, and inserting the iv tubing via a rapid infusion catheter into a readily available vein consistent with normal blood infusion protocols, and adjusting millimeters of mercury/flow rate using the pump pressure sensitivity sliding dials according to how profuse the wound is hemorrhaging and recirculator apparatus efficiency. That is, blood is returned to the body via multi access catheter and/or consistent with present and future rapid infusion procedural methods that could change according to severity of injuries and the need for alternate vascular access points and/or infusion delivery protocols.

In the procedure, there may be additional infusion ports. The flow rate may be adjusted in accordance with how much the wound is bleeding. The flow rate may be from about 2 ml/min to about 2500 ml/min. There may be 2 vacuum pumps and 3 infusion pumps.

BRIEF DESCRIPTION OF THE DRAWINGS

The present disclosure will now be described more fully hereinafter with reference to the accompanying drawings, in which embodiments of the disclosure are shown. However, this disclosure should not be construed as limited to the embodiments set forth herein. Rather, these embodiments are provided so that this disclosure will be thorough and complete, and will fully convey the scope of the disclosure to those skilled in the art. Like numbers refer to like elements throughout.

FIG. 6 depicts the adhesive vacuum attachment unit according to the disclosure.

FIG. 8A depicts a continuation of the process of treating a bleeding wound according to the disclosure.

DETAILED DESCRIPTION

For simplicity and illustrative purposes, the present disclosure is described by referring mainly to exemplary embodiments thereof. In the following description, numerous specific details are set forth in order to provide a thorough understanding of the present disclosure. However, it will be readily apparent to one of ordinary skill in the art that the present disclosure may be practiced without limitation to these specific details.

Recovery and reinfusion of blood from surgical drains is a commonly used technique to avoid transfusion of allogeneic blood. The primary function of these devices is to act as a reservoir for the shed blood. When adequate amounts of blood are collected, the system is flipped over and plugged into an intravenous line. This procedure has earned these devices the nickname of "flip-n-drip" systems. They are composed of an inlet which is connected to the wound drain, gross filtration (typically between 100 and 200 microns), a collection reservoir, and an access port for an intravenous administration set. The more sophisticated of these devices add vacuum control, fat-specific filtration, a label, an anti-air embolism valve, a check valve and a port for the possible addition of an anticoagulant. Typically, the blood is collected, filtered and reinfused without washing. The anti-air embolism valve can optionally be present inside the apparatus as well.

However, these devices are not suitable for use in emergency situations. A hemorrhaging wound at the site of an accident will not only emit blood but also will emit bits of flesh, bone, cartilage and clotted blood which will overwhelm a conventional flip-n-drip system. These systems are not portable for use in ambulances, emergency vehicles, police cars, etc. in a non-hospital operating room environment.

The disclosure is related to a portable apparatus and method to treat profusely bleeding wounds by collecting the blood in a reservoir and then injecting the collected blood back into the patient. Pertinent parameters include the blood pressure of the patient, temperature of the blood, blood vacuuming speed, blood injection speed and the tendency of the blood to clot. These issues are addressed in the disclosure.

Figure 1:
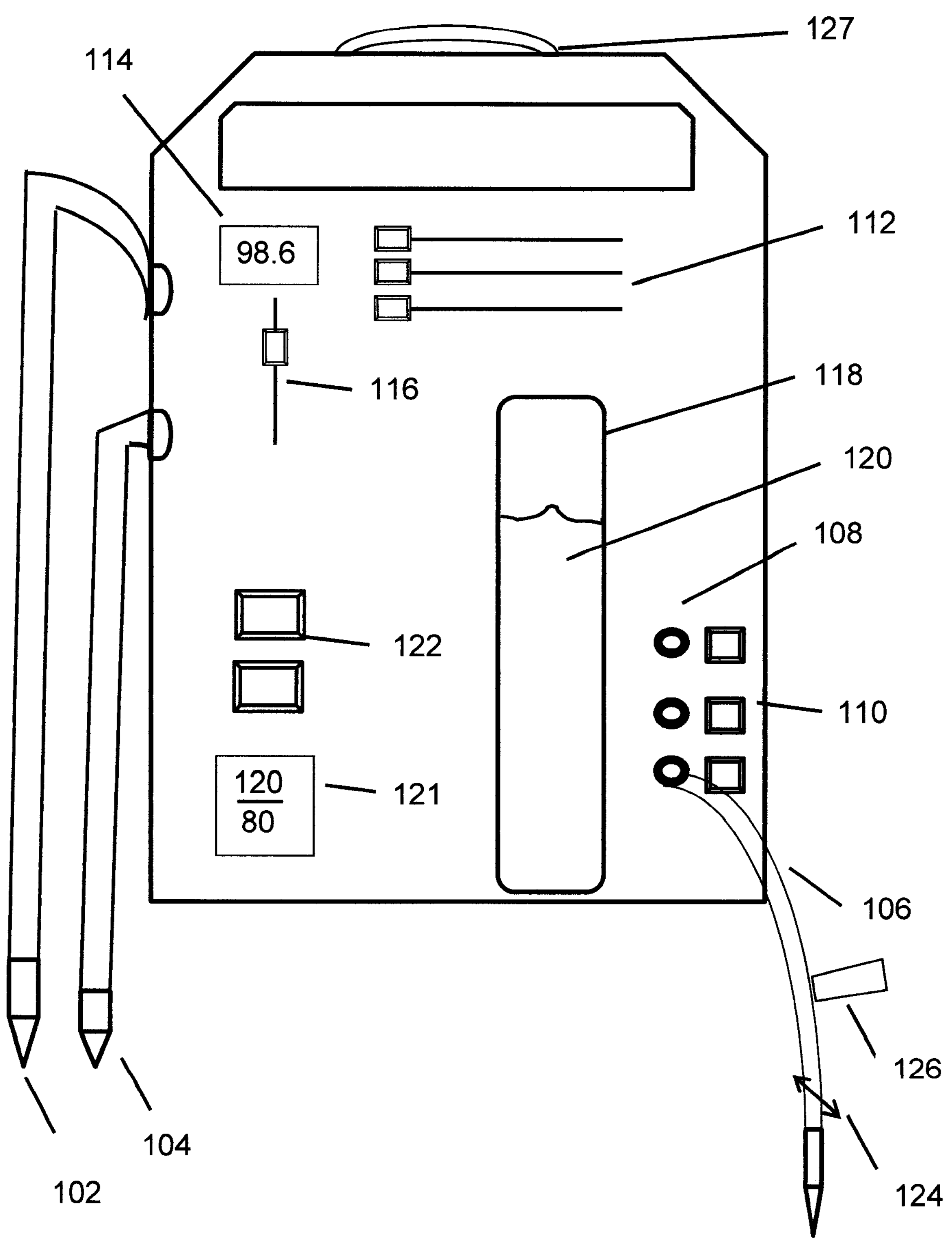
FIG. 1 depicts the outer casing of the wound treating apparatus according to the disclosure.
Figure 7:
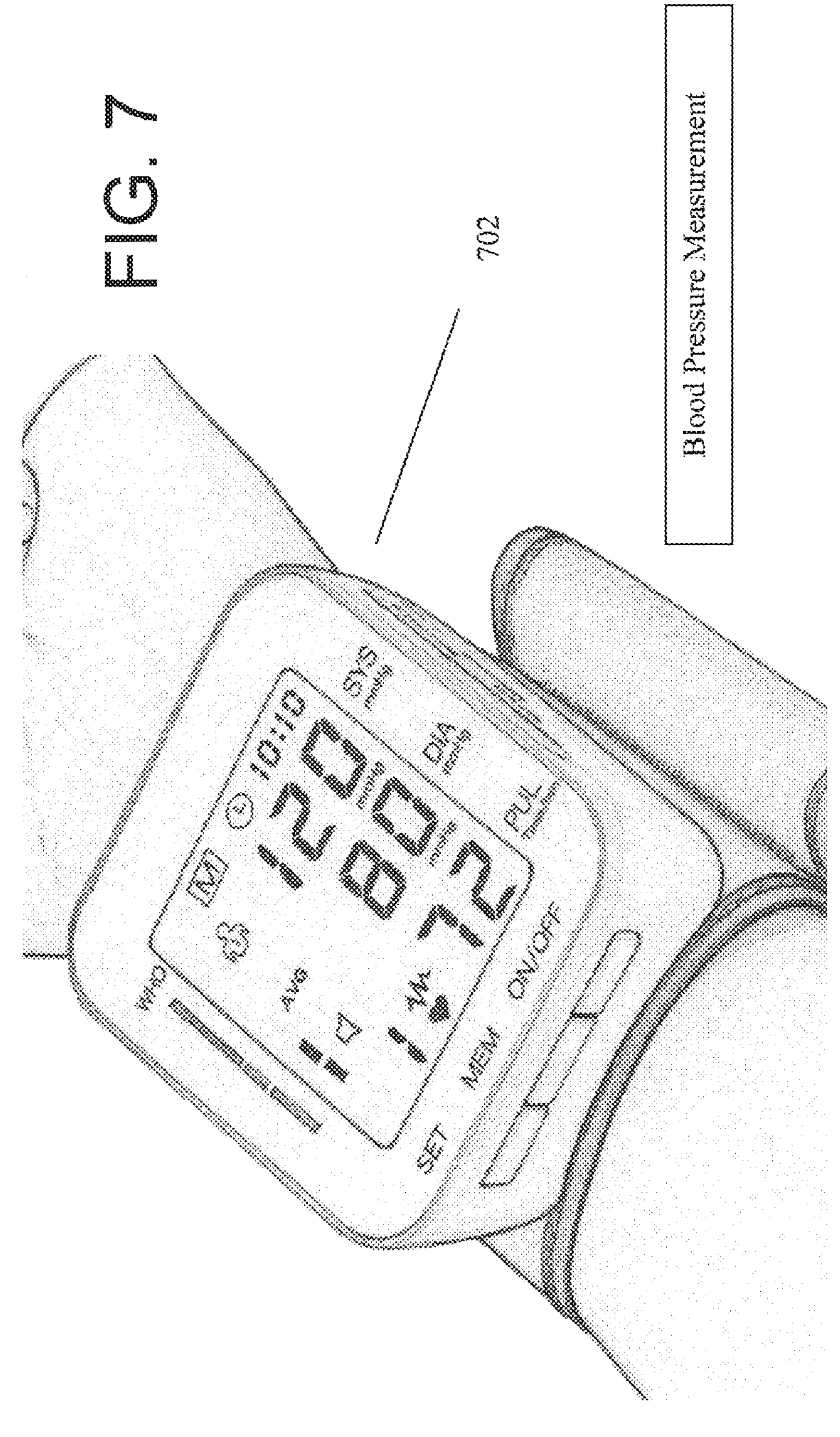
FIG. 7 depicts a Bluetooth enabled blood pressure cuff according to the disclosure.

FIG. 1 shows the outside of the wound treating apparatus according to an embodiment of the disclosure. The apparatus includes vacuum hoses 102, 104 for removing blood from a wound. There is at least one infusion catheter or iv tubing 106 for returning the blood to the patient. The catheter may include a vacuum safety lever 124 and a dual port catheter adapted for the injection of an anti-clotting agent such as heparin. FIG. 1 shows three exit ports 108, each having an infusion pump switch 110. The unit includes pressure regulator switches or pressure sensitivity sliding dials 112 to regulate the pressure in the respective catheter or iv tubing 106. Temperature of the blood in the unit is maintained by a temperature regulator 116, with the temperature being indicated by the temperature gauge 114. A window 118 permits a view of a transparent plastic reservoir 120. Blood pressure is measured using a blood pressure monitor optionally having a Bluetooth or similar wireless connect to a blood pressure cuff 702 on the patient's wrist, as is shown in FIG. 7. The blood pressure display 121 is optional. Vacuum is turned on and off using the vacuum pump switches 122. The vacuum may be constant. The apparatus is portable so it can be removed from an emergency vehicle to treat the bleeding patient in situ. A mini-version can be attached to the belt of a policeman or EMT technician. The size of the portable unit may be about 8 inches by about 12 inches by about 5 inches. The mini version may be about 4 inches by about 6 inches by about 3 inches.

Figure 9:
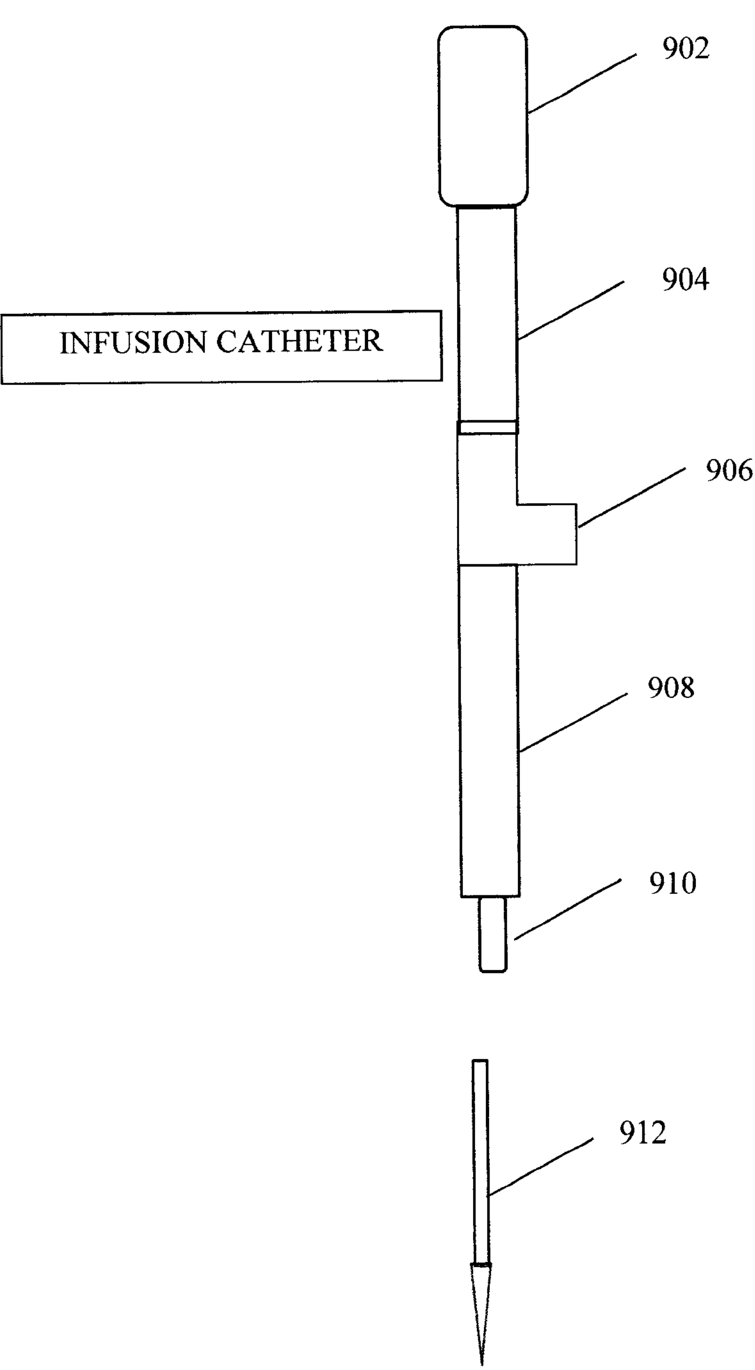
FIG. 9 depicts an infusion catheter assembly.

Details of the infusion catheter are shown in FIG. 9. Male head 902 is adapted for insertion into a female insertion port of the respective infusion pump. Upper catheter 904 leads to a dual port or multiple access iv catheter 906 that can be utilized to inject anticoagulant such as heparin or saline solution into the infusion. Dual port or multiple access iv catheters are typically manufactured by Becton Dickinson (BD). Lower catheter 908 leads to a male port adapted to be fitted to the female infusion iv needle 912. In an embodiment, smart connection could be used as well instead of male to female connectivity.

Figure 10:
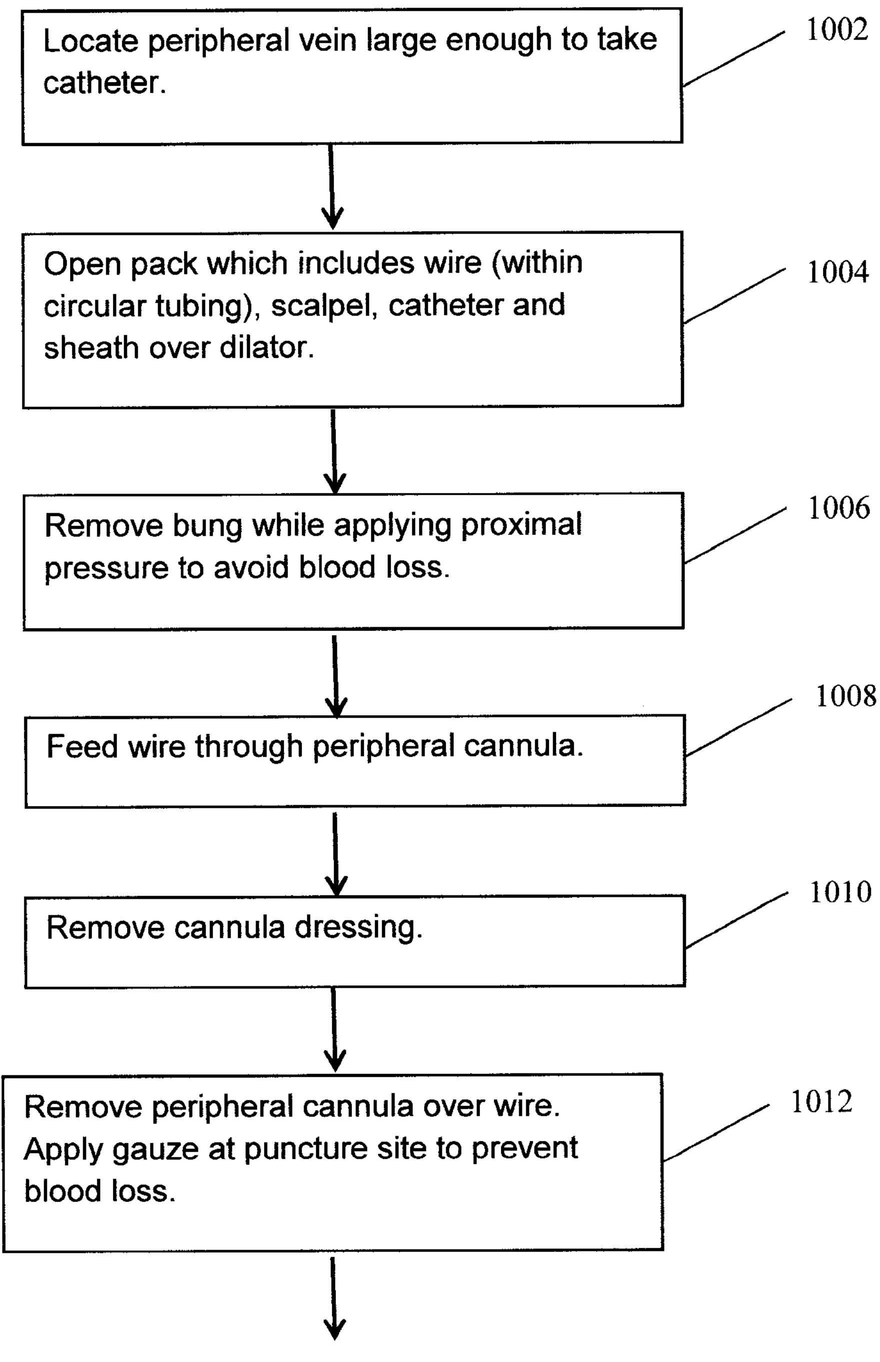
FIG. 10 depicts a rapid infusion protocol using the infusion catheter of FIG. 9.
Figure 10A:
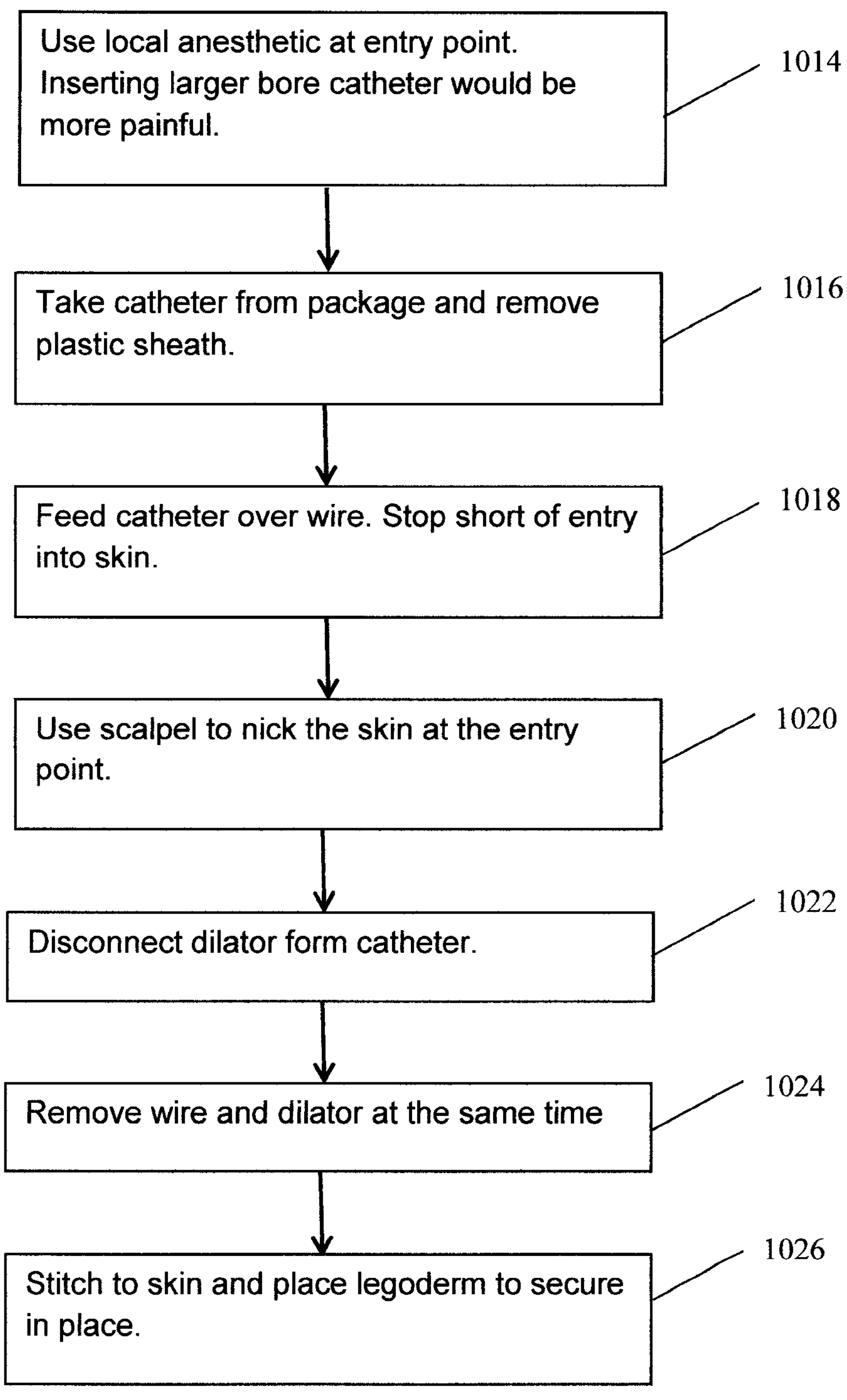
FIG. 10A depicts a continuation of the rapid infusion protocol of FIG. 10.

FIG. 10 and FIG. 10A depict a rapid infusion protocol using, e.g., the infusion catheter of FIG. 9. In step 1002 the technician locates a peripheral vein large enough to take catheter. Step 1004 is to open the pack which includes wire (within circular tubing), scalpel, catheter and sheath over dilator. Step 1006 is to remove the bung while applying proximal pressure to avoid blood loss. Next, in step 1008, the wire is fed through the peripheral cannula. Then the cannula dressing is removed in step 1010. In step 1012 the technician removes the peripheral cannula over the wire and applies gauze to the puncture site to prevent blood loss.

In step 1014, as shown in FIG. 10A, the technician applies local anesthetic at the entry point since inserting a larger catheter would be more painful. In step 1016 the catheter is removed from the package and the plastic sheath is removed. In step 1018 the catheter is fed over the wire, stopping short of entry into the skin. Then in step 1020 a scalpel is used to nick the skin at the entry point. This will facilitate passage of a large bore catheter through the skin. In step 1020 the dilator is disconnected from the catheter. Then, in step 1024, the wire and dilator are removed at the same time, leaving the catheter in-situ within the vein. In step 1026, stitch to the skin and place the legoderm to secure the bioconnector in place. Not reapplying the bioconnector/tubing allows faster infusions. In some circumstances the blood would need to be heated before reinfusion, which should be almost instantaneous. Heating the blood in the procedural process could be determined by the technician or administrator, and what particular order to apply during the procedure.

Figure 11:
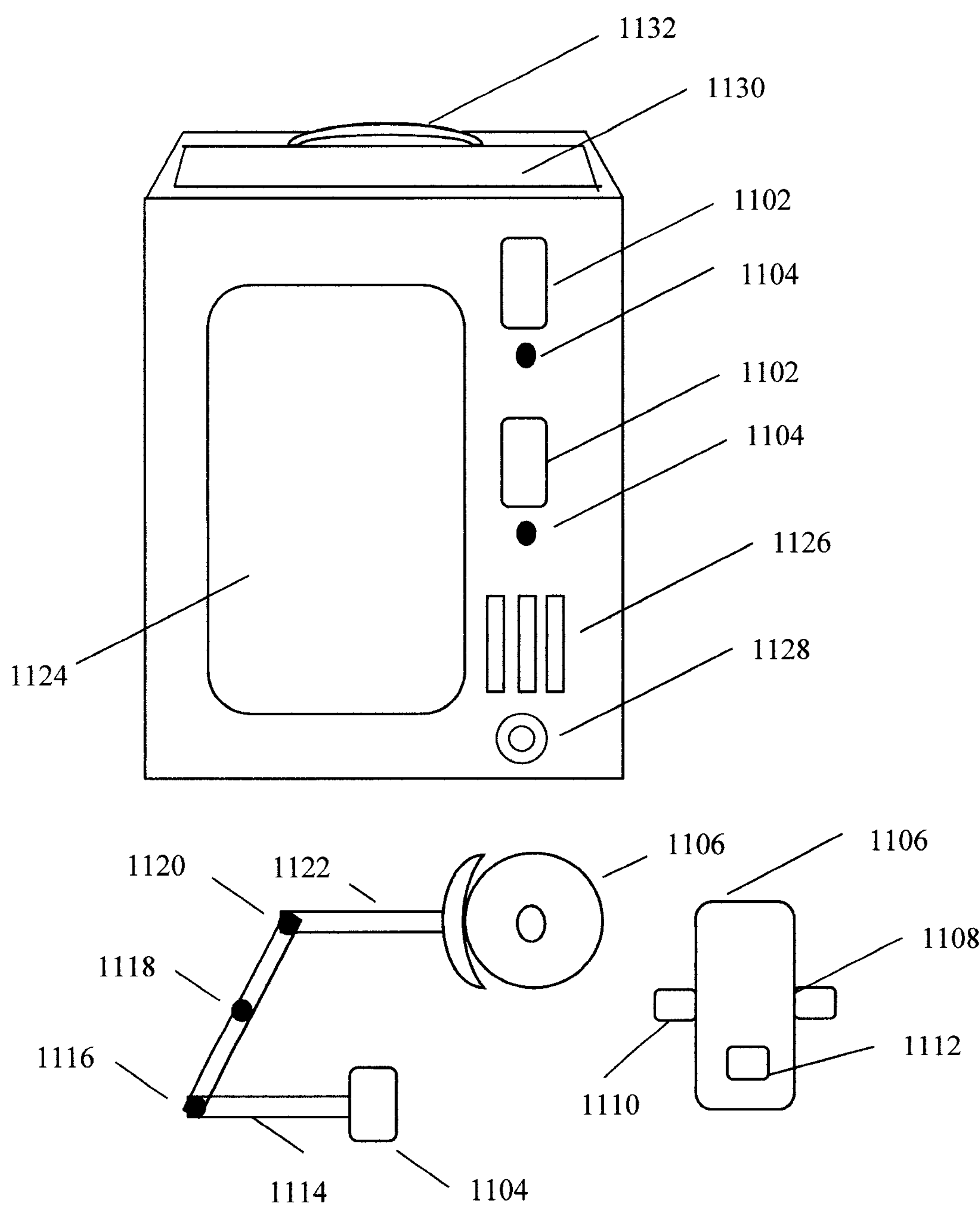
FIG. 11 depicts the rear of the wound treating apparatus, a quick release filter and a quick release mechanism.

FIG. 11 depicts the rear of the apparatus having at least 2 openings 1102 and ejection buttons 1104 on the rear of the casing. The quick release filter 1106 has an inlet 1108 and an outlet 1110. The inlet and the outlet may be quick connection fittings with a push-fit locking design such as are manufactured by Parker. The filter 1106 may be equipped with a heater 1112 that may be battery powered. The ejection mechanism has the button 1104 attached to a first member 1114 attached to a hinge 1116 connected to a second member with a pivot 1118. The pivot 1118 may be attached to the side of the casing in order to stabilize the ejection mechanism. The pushing element 1122 is attached to the second member 1118 with a hinge 1120 via a hinge 1120. The ejection mechanism can be made from plastic or steel. A door 1124 allows access to the reservoir so as to permit a quick change-out. The unit itself may have color coded/changing bile test strips or indicators 1126 to let administrators of this technology know if infusion specimens have been contaminated. The apparatus may have a power port 1128 that can be covered for water or fluid resistance. A power cord may be plugged into the power port 1128 for seamless battery operation and power cord operation. An opening or door 1130 is at the top of the apparatus to permit access to the reservoir. The opening or door 1130 may be folded open using the handle 1132.

Quick ejection of the filter 1106 is necessary because of the frequently gory nature of a hemorrhaging wound. Not only blood is vacuumed up, but also flesh, bone, cartilage and clotted blood. This will result in the frequent clogging of the filter, thus making a quick change of the filter necessary. Using the quick release filter will permit changing the filter in about 5 to about 10 seconds. Having more than one vacuum line permits continued vacuuming of hemorrhaging blood while the filter is being changed out. The filter element inside the quick release filter 1116 may be an about 2 to about 300 micron heated aluminum/steel mesh. Other typical pore sizes include about 100 microns to about 200 microns. The filter change is performed by turning off the vacuum applied to the clogged filter, disconnecting the quick connect filter inlet and outlet, ejecting the filter, and fitting the new filter to the line. Afterwards, the vacuum can be turned back on.

Figure 2:
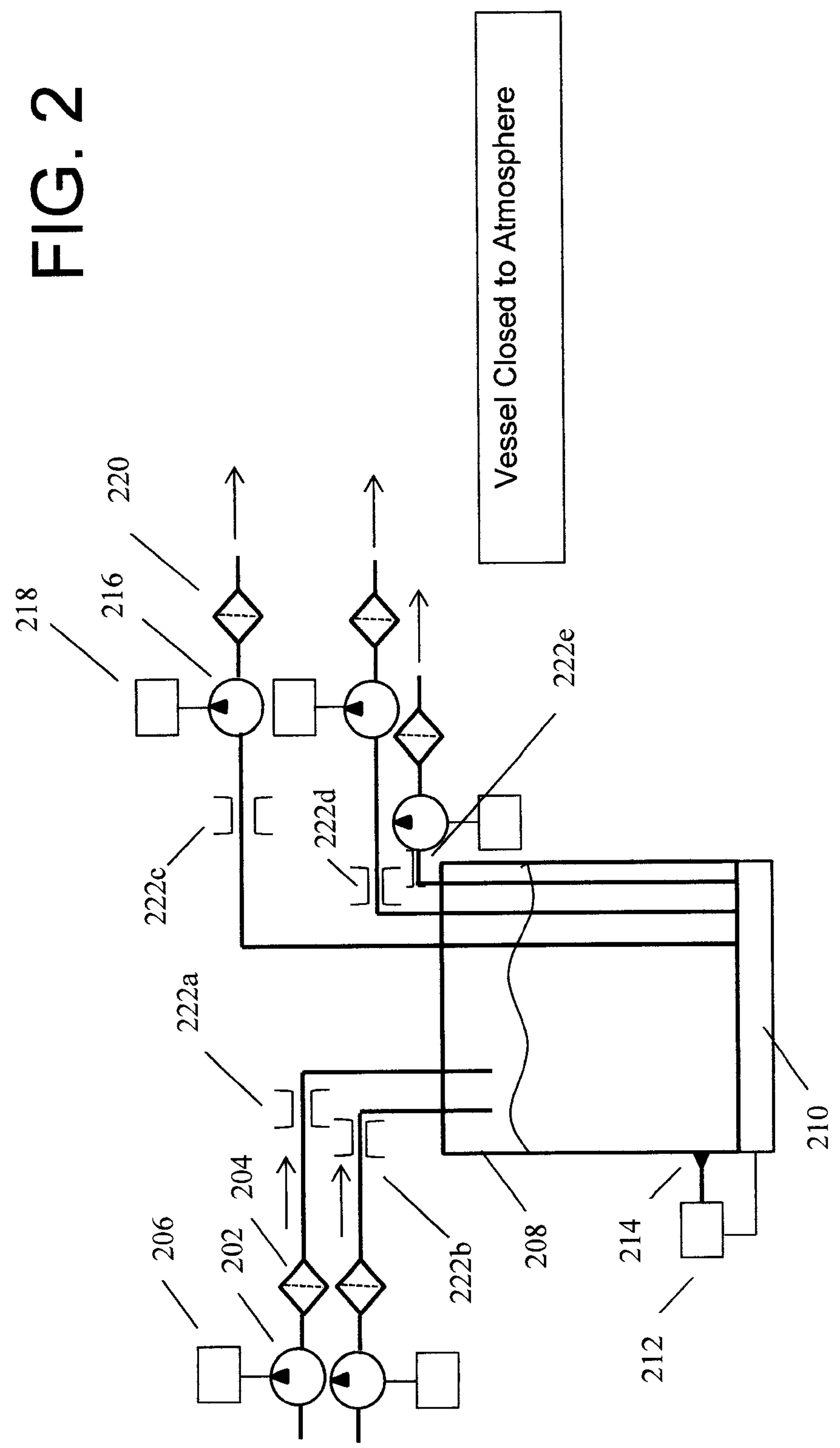
FIG. 2 depicts the schematic of the wound treating apparatus with closed to the atmosphere apparatus according to the disclosure.

FIG. 2 is a schematic diagram of an embodiment of the disclosure where the reservoir 208 is closed to the atmosphere. Blood is collected from the wound using a vacuum pump 202, which is upstream from a replaceable, ejectable filter 204. The vacuum pump controller 206 is adapted for either manual or computer controlled operation. The transparent plastic reservoir is fitted with a heater 210 and temperature measuring element 214 such as a thermocouple. The heat controller 212 can be operated either manually or by a computer. Blood is returned to the patient from the reservoir 208 using at least one infusion pump 216, downstream of which is a replaceable filter 220. The infusion pump controller 208 permits either manual control or computer steered control. Pressure in the system is maintained using pressure regulators 222*a*, 222*b*, 222*c*, 222*d* and 222*e*.

Figure 3:
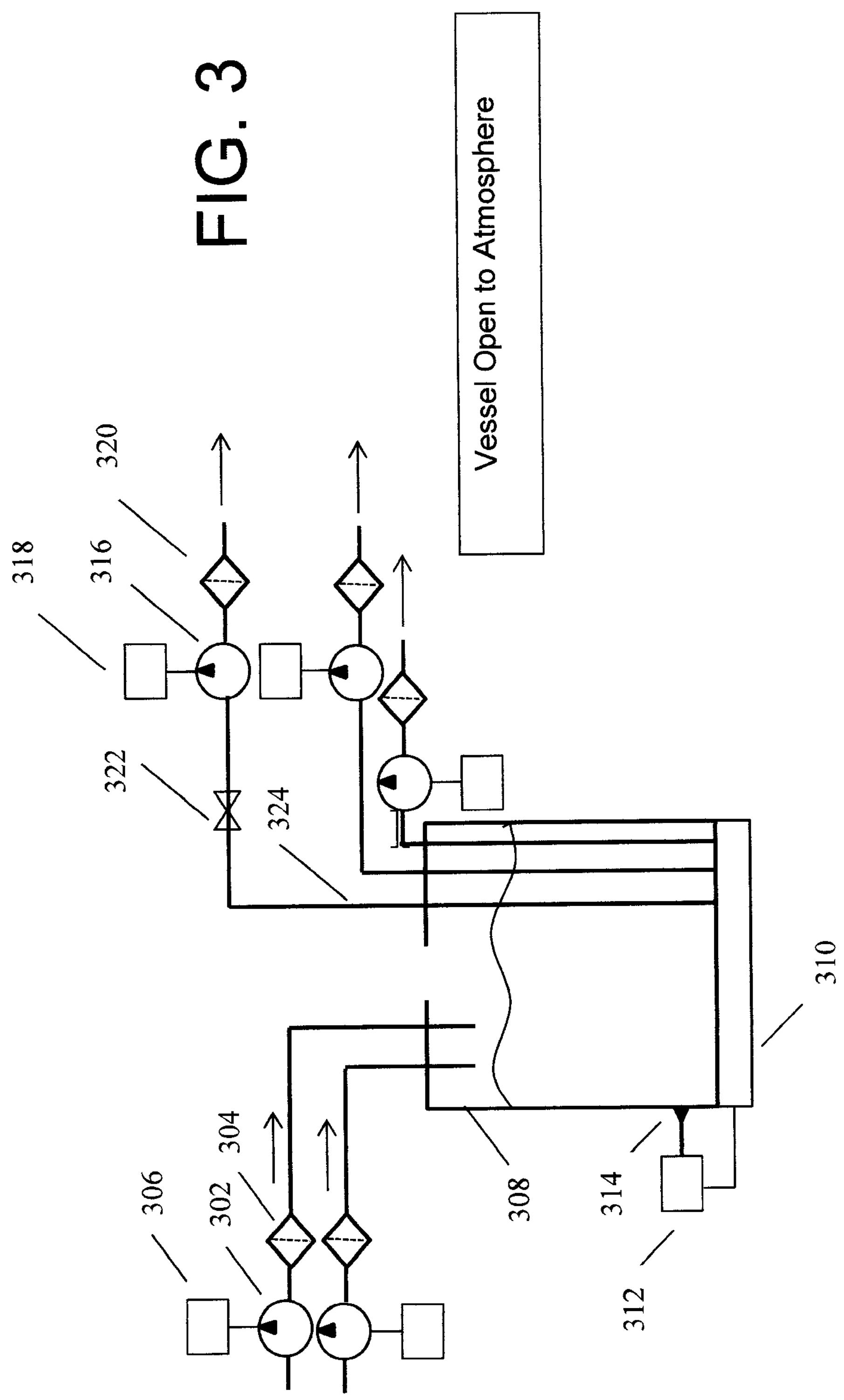
FIG. 3 depicts the schematic of the wound treating apparatus with open to the atmosphere apparatus according to the disclosure.

FIG. 3 shows an embodiment in which the transparent plastic reservoir 308 is vented to the atmosphere. Blood is collected from the wound using a vacuum pump 302, which is upstream from a replaceable filter 304. The vacuum pump controller 306 is adapted for either manual or computer controlled operation. The transparent plastic reservoir is fitted with a heater 310 and temperature measuring element 314 such as a thermocouple. The heat controller 312 can be operated either manually or by a computer. Blood is returned to the patient from the reservoir 308 using at least one infusion pump 316, downstream of which is a replaceable filter 320. An air embolism inhibitor 322 may be install at any point in the line, either upstream or downstream of pump 316 and replaceable filter 320. The infusion pump controller 318 permits either manual control or computer steered control. Three infusion pumps are shown, but there is no limit to the number of infusion pumps. For example there may be 2, 4 or 5 infusion pumps in the embodiments of the disclosure. The line 324 from each infusion pump may be configured to reach the bottom of the reservoir. Also, the system can be treated so as to be water resistant.

Figure 4:
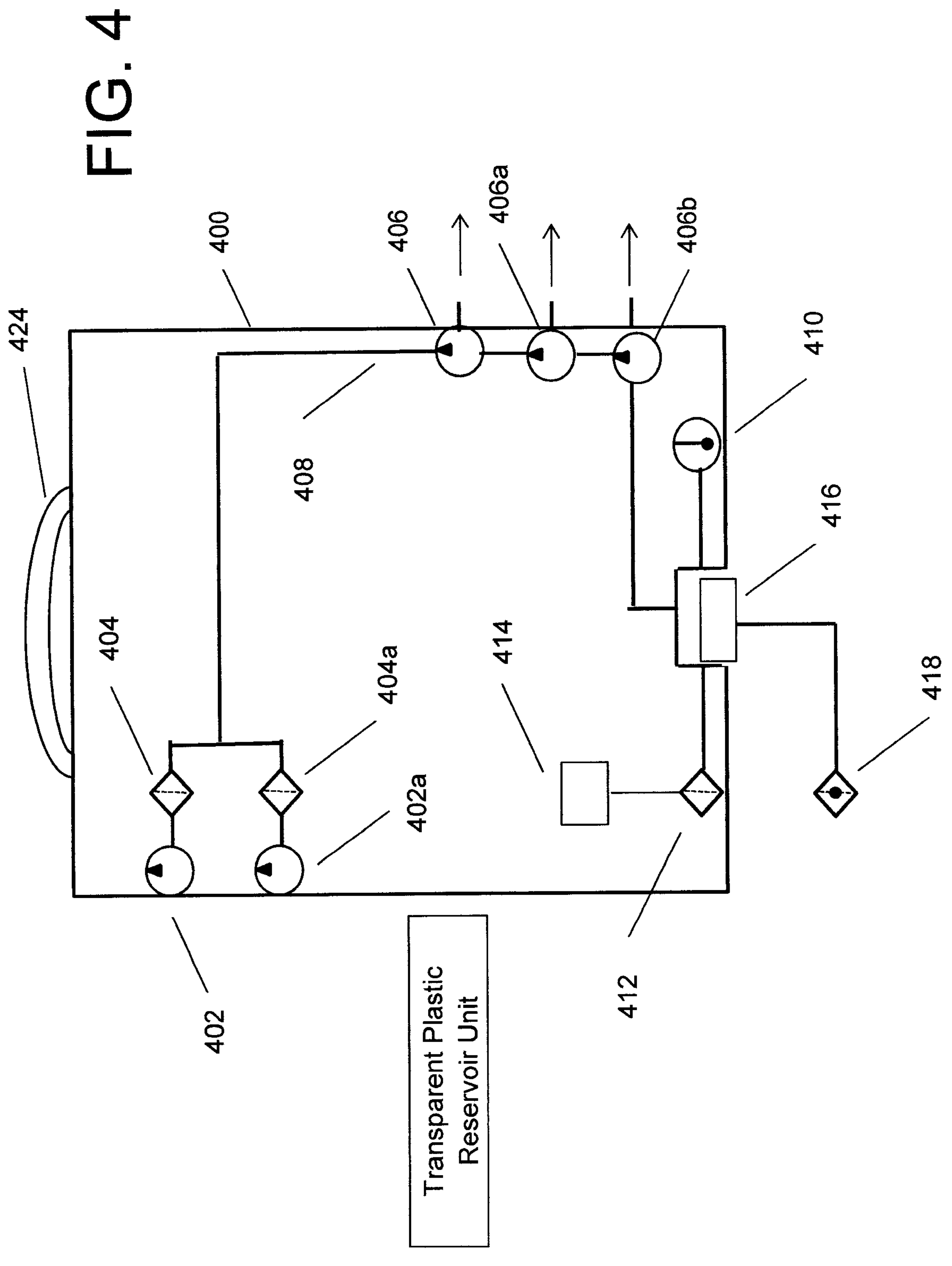
FIG. 4 depicts the transparent reservoir unit of the wound treating apparatus according to the disclosure.
Figure 4A:
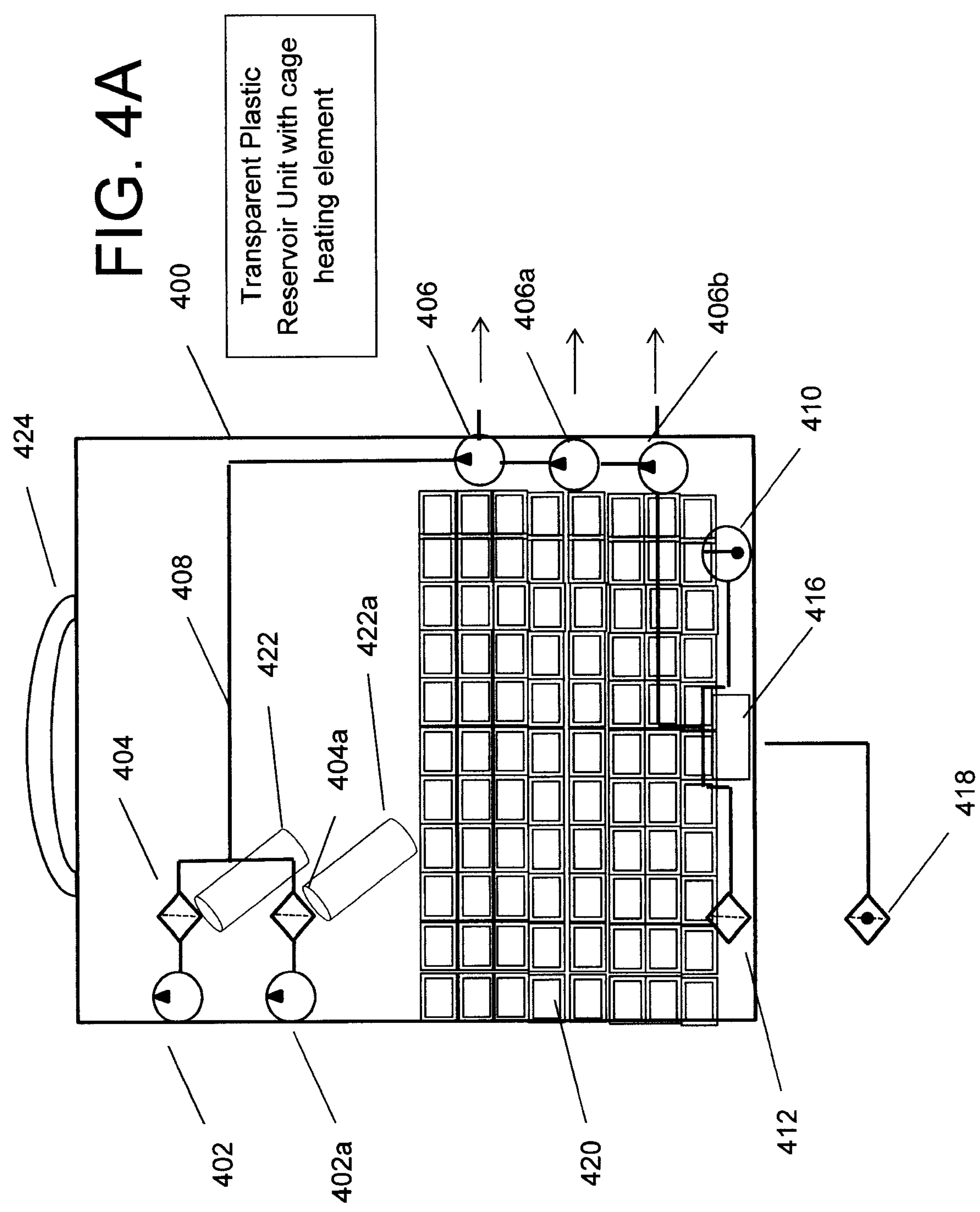
FIG. 4A depicts the transparent reservoir unit of the wound treating apparatus with a heating cage according to the disclosure.

FIG. 4 is a schematic of a transparent plastic reservoir 400 according to an embodiment of the disclosure. Vacuum pumps 402, 402*a* are adapted to remove, via a vacuum hose, blood from the wound. Vacuum hoses are attachable and detachable. Downstream from the vacuum pumps 404, 404*a*, are replaceable, ejectable blood filters 404, 404*a*, flow cylinders 422, 422*a* direct blood into the reservoir, as are shown in FIG. 4A. Blood is returned to the patient using rapid infusion pumps 406, 406*a*, 406*b*. In this embodiment, the infusion pumps are inside the plastic reservoir. The reservoir is fitted with a temperature sensor 410, a heat controller 412 and a heating element 414. A female power port or smart connection port 416 allows access to a power supply such as a battery. The female power port or smart connection 416 also allows access to an outside controller such as a computer. The handle 424 aids portability and removability of the reservoir.

FIG. 4A shows the transparent plastic reservoir 400 with a 3 dimensional grid or cage heating element 420. The grid or cage heating element is typically nichrome 80/20 (80% nickel, 20% chromium) covered with polyimide or silicone polymer. Other heating element materials include FeCrAl wire or cupronickel (CuNi) alloys. Other elements of this configuration include vacuum pumps 404, 404*a*, and replaceable blood filters 404, 404*a*. Flow cylinders 422, 422*a* direct blood into the reservoir. Blood is returned to the patient using rapid infusion pumps 406, 406*a*, 406*b*. In this embodiment, the infusion pumps are inside the plastic reservoir. The reservoir is fitted with a temperature sensor 410 and a manual or computer controlled heat controller 412. A female power port or smart connection 416 allows access to a power supply such as a battery. The female power port 416 also allows access to an outside controller such as a computer. Battery types include alkaline batteries, lithium batteries, carbon zinc batteries, silver oxide batteries, zinc air batteries and nickel cadmium batteries. The battery may also be a high capacity capacitive battery such as a graphene supercapacitor.

The infusion pumps of the disclosure are adjustable flow rate rapid infusion pumps that can pump at a rate of from about 2 ml/min to about 2500 ml/min. Infusion pumps may be powered electrically or mechanically. Different pumps operate in different ways. For example, in a syringe pump, fluid is held in the reservoir of a syringe, and a moveable piston controls fluid delivery. In an elastomeric pump, fluid is held in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates. A "smart pump" is equipped with safety features, such as user-alerts that activate when there is a risk of an adverse drug interaction, or when the user sets the pump's parameters outside of specified safety limits.

The blood filters of the disclosure may be a replaceable heated about 100 or about 200 micron aluminum or steel mesh. The range of possible pore sizes is from about 2 microns to about 300 microns. Alternatively, a commercially available replaceable blood filter can be utilized, such as is manufactured by Pall Biomedical Products Company. An exemplary blood transfusion filter is Pall's 40 micron rated polyester screen media, which provides protection from microaggregates, clots and particulate debris from stored or salvaged blood components, and has low residual blood hold-up volume and minimal blood trauma. The pore size of the filter is not necessarily restricted and can range from about 20 microns to about 300 microns in 10 micron increments. Also, two or more filters can be used with the coarser filter upstream and the finer filter downstream.

The vacuum pumps provide the suction necessary to remove blood from the wound. The vacuum may be constant. The vacuum can be at different settings, for example about 50, about 80 or about 125 mm Hg. Different types of pumps can be used to provide the negative pressure, for example a rotary vane pump or a peristaltic pump. The vacuum hoses may have a diameter from about 1 inch to about 2 inches. A typical length of the vacuum hose can be about 6 feet. The material for the hydrophobic vacuum hoses can be formed from polyvinyl chloride (PVC), thermoplastic elastomer (TPE), silicone or fluoropolymers. The tubing should offer compliance with FDA, USP, NSF and other standards needed for compliance in certain medical device applications.

The catheter or iv tubing needle for returning the blood to the body may be an 8 gauge needle is standard, but a needle or catheter as small as 23-gauge can be used for transfusion if necessary. The smaller the gauge, the slower is the flow rate and the higher is the risk of clotting. The most common sizes range from 14 to 22 gauge. The higher the gauge number, the smaller the cannula. The tubing may be formed from polyvinyl chloride (PVC), thermoplastic elastomer (TPE), silicone or fluoropolymers. Standard blood transfusion tubing sets can be used. These may include an in-line microaggregate filter (about 170-260 micron filter).

Heparin or saline solution can be injected into the catheter via a dual port catheter, such as are manufactured by Becton Dickinson or Teleflex. Heparin can come in various solutions: about 1 unit/ml, about 2 units/ml, about 10 units/ml or about 100 units/ml. In the body, Heparin is usually stored within the secretory granules of mast cells and released only into the vasculature at sites of tissue injury. It has been proposed that, rather than anticoagulation, the main purpose of heparin is defense at such sites against invading bacteria and other foreign materials. The anticoagulant is not restricted to heparin. Other anticoagulants may be used, such as apixaban, dabigatran, edoxaban, rivaroxaban or warfarin.

The temperature sensor measures the temperature of the blood in the reservoir. Examples of temperature sensors include thermocouples, resistive temperature devices (RTDs), thermistors, infrared radiators, bimetallic devices, liquid expansion devices, molecular change-of-state and silicon diodes. The heater inside the reservoir can be semiconductor based. Another type of heater is a polyimide insulated flexible heater, such as is manufactured by Omega Engineering or Birk.

The device works in conjunction with fluid resuscitation methods; delivering colloids and infusion of unwashed shed blood, while allowing the administration of various drugs via multiple, attachable multi access catheters.

Figure 5:
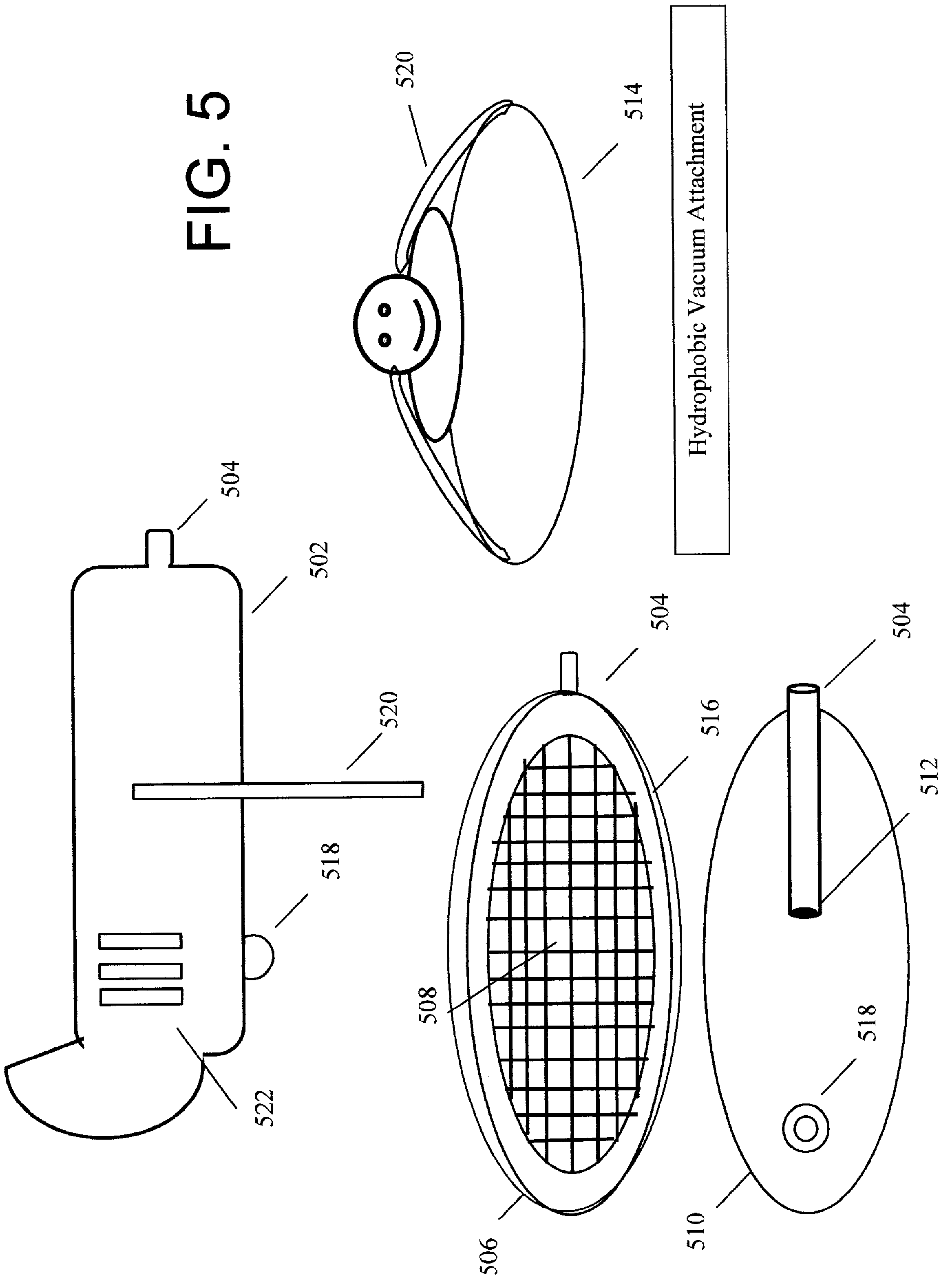
FIG. 5 depicts the hydrophobic vacuum attachment unit of the wound treating apparatus with closed to the atmosphere apparatus according to the disclosure.

FIG. 5 depicts a hydrophobic pillow-like vacuum attachment for removing blood from a chest wound. The side view 502 shows the side of the hollow cushion and a vacuum connection port 504. The top view 506 includes a drain including hard surfaces 508 that is connected to the vacuum connection port 504. The bottom view 510 shows the vacuum connection port 504 including an air vent 512. The front view 514 shows the orientation of the patient on the hydrophobic vacuum attachment. The hard surfaces protrude from the center of the pillow-like vacuum attachment so than an injured person can lay on it to use their body weight to apply pressure. This center piece can be adjusted out of the way as well. An adhesive layer 516 may aid in adhering the vacuum attachment to the chest. The adhesive may be an acrylic, a cyanoacrylate or a silicone adhesive. Optionally, the adhesive can be light cured. The adhesive may have a thickness of from about 25 microns to about 200 microns. A typical adhesive thickness may be 150 microns. The hydrophobic vacuum attachment is also fitted with an adjustable VELCRO (a synthetic material sold in ribbon, sheet, or piece goods form, said material having complemental parts which adhere to each other when pressed together and adapted for use as a closure fastener, or button for closing garments, curtains, or the like; separable fasteners-namely, hook and loop-type fasteners and components thereof) strap(s). The adjustable VELCRO strap(s) is adapted to meet end to end so that when trying to transport a victim, the attachment is secured to the back, torso or abdomen, when lifting and moving a victim. The vacuum attachment includes a cap 518 to close the vacuum attachment on the pillow attachment to hold the leaking blood of a victim. The cap 518 on the pillow like vacuum attachment permits it to be distributed and used on accident or violent scenes to hold the blood of a bleeding accident or violent attack victim until someone arrives on scene to reinfuse the shed blood and administer colloids or crystalloids if necessary. The center part of the pillow vacuum attachment can be adjusted out of the way. The curved design to the the left of the vent(s) is optional. The pillow vacuum attachment may have a uniform oval shape with a VELCRO strap on each end. The pillow vacuum attachment, as well as the unit itself, may have color coded/changing bile test strips or indicators 522, 1026 (see FIG. 10) to let administrators of this technology know if infusion specimens have been contaminated. The hydrophobic vacuum attachment provides advantages in that when applying pressure to a wound in the chest, ribs or upper torso, there would be little or no further injury to areas where bones are broken from blunt force trauma.

Figure 6:
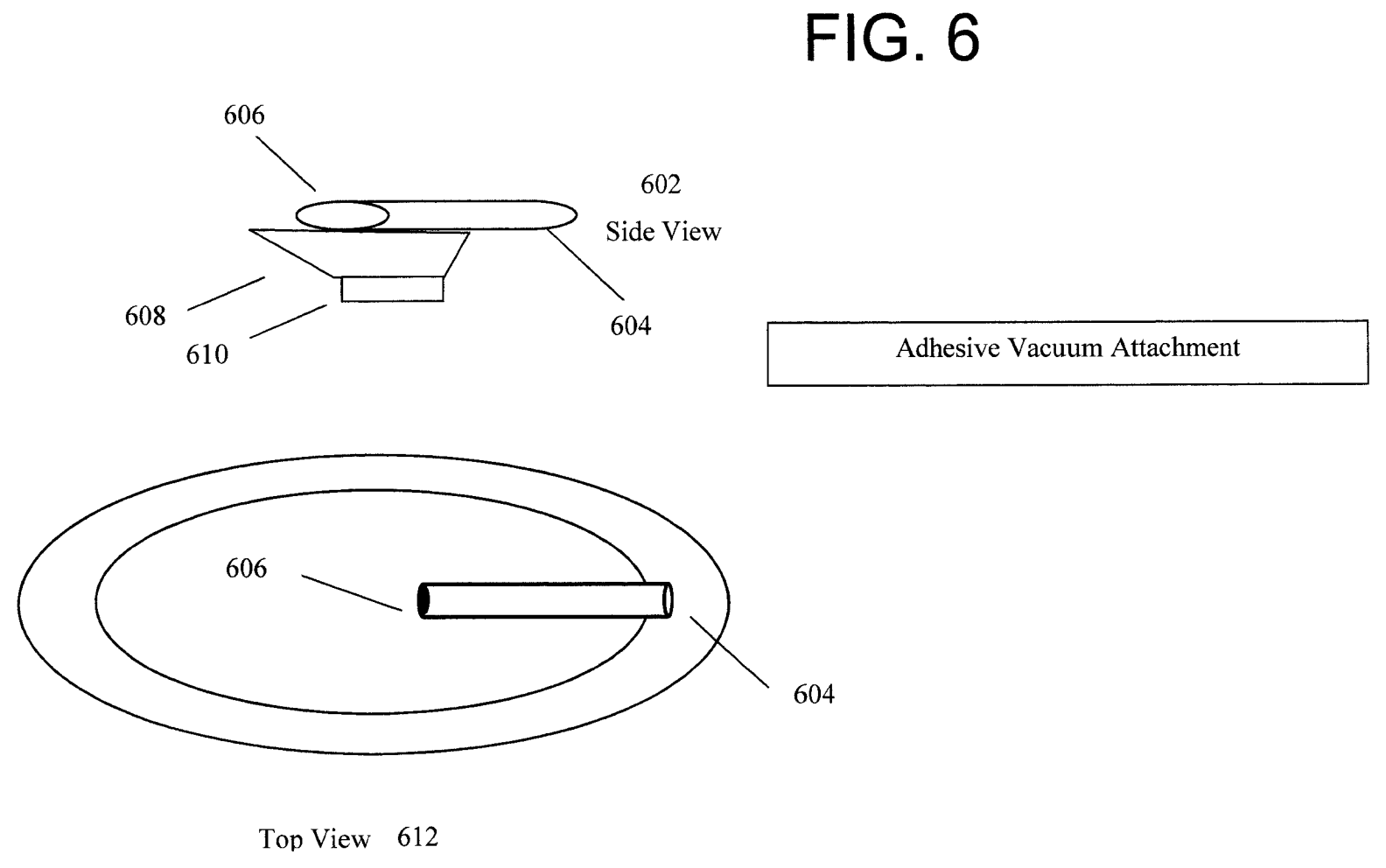

FIG. 6 depicts an adhesive vacuum attachment for smaller wounds. The side view 602 shows a vacuum connection point 604, and an air vent 606. A suction head 608 is attached to the patient using a layer of adhesive 610. The adhesive may be an acrylic, a cyanoacrylate or a silicone adhesive. Optionally, the adhesive can be light cured. The adhesive may have a thickness of from 25 microns to 200 microns. A typical adhesive thickness may be 150 microns on a polyester substrate. The materials of the attachments of FIG. 5 and FIG. 6 may be polyester, polypropylene or PVC. The suction head 608 may have a diameter of about 0.5 inch, about 1 inch, about 1.5 inches, about 2 inches, about 3 inches or about 4 inches. In a typical application, the suction head may have a dimension of about 2 inches by about 4 inches. Different size suction heads may be selected for different size wounds. Similar to the hydrophobic vacuum attachment discussed above, the adhesive vacuum attachment provides advantages in that when applying pressure to a wound in the chest, ribs or upper torso, there would be little or no further injury to areas where bones are broken from blunt force trauma.

FIG. 7 shows a blood pressure cuff 702 optionally fitted with Bluetooth or other wireless communication adapted to communicate with the blood pressure gauge or display of the wound treating apparatus of the disclosure. Other communication options include induction wireless that permits the transfer of data, audio and voice from one device to another. Induction wireless uses magnetic induction rather than radio for close-range communications. In radio, both electric and magnetic fields make up the signal, while in induction wireless, only the magnetic field is transmitted. The transmitter is a radiating coil that's more like the primary winding of a transformer than an antenna. Another alternative to Bluetooth is using a near-field communication (NFC) chip.

Figure 8:
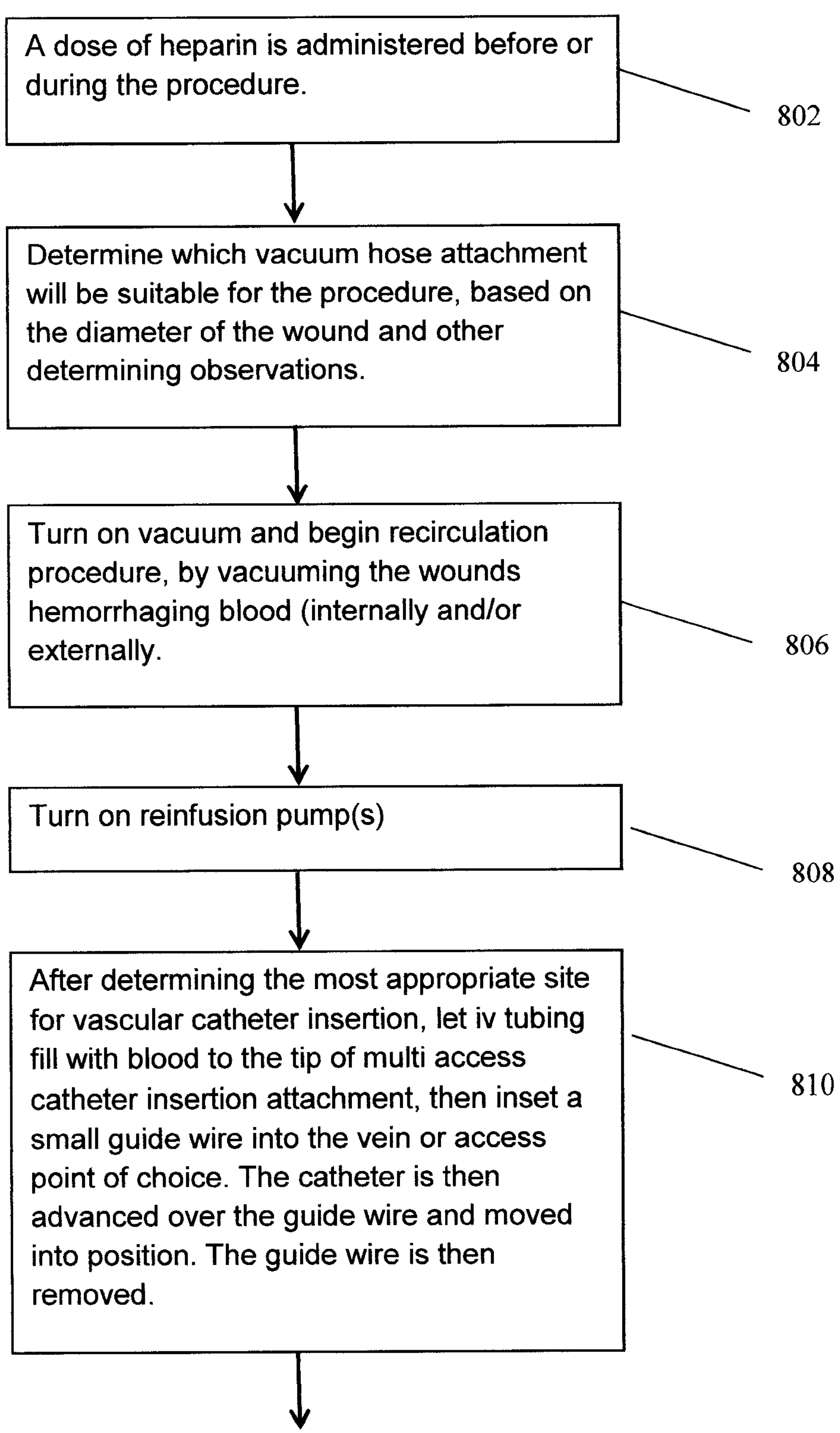
FIG. 8 depicts a process of treating a bleeding wound according to the disclosure.
Figure 8A:
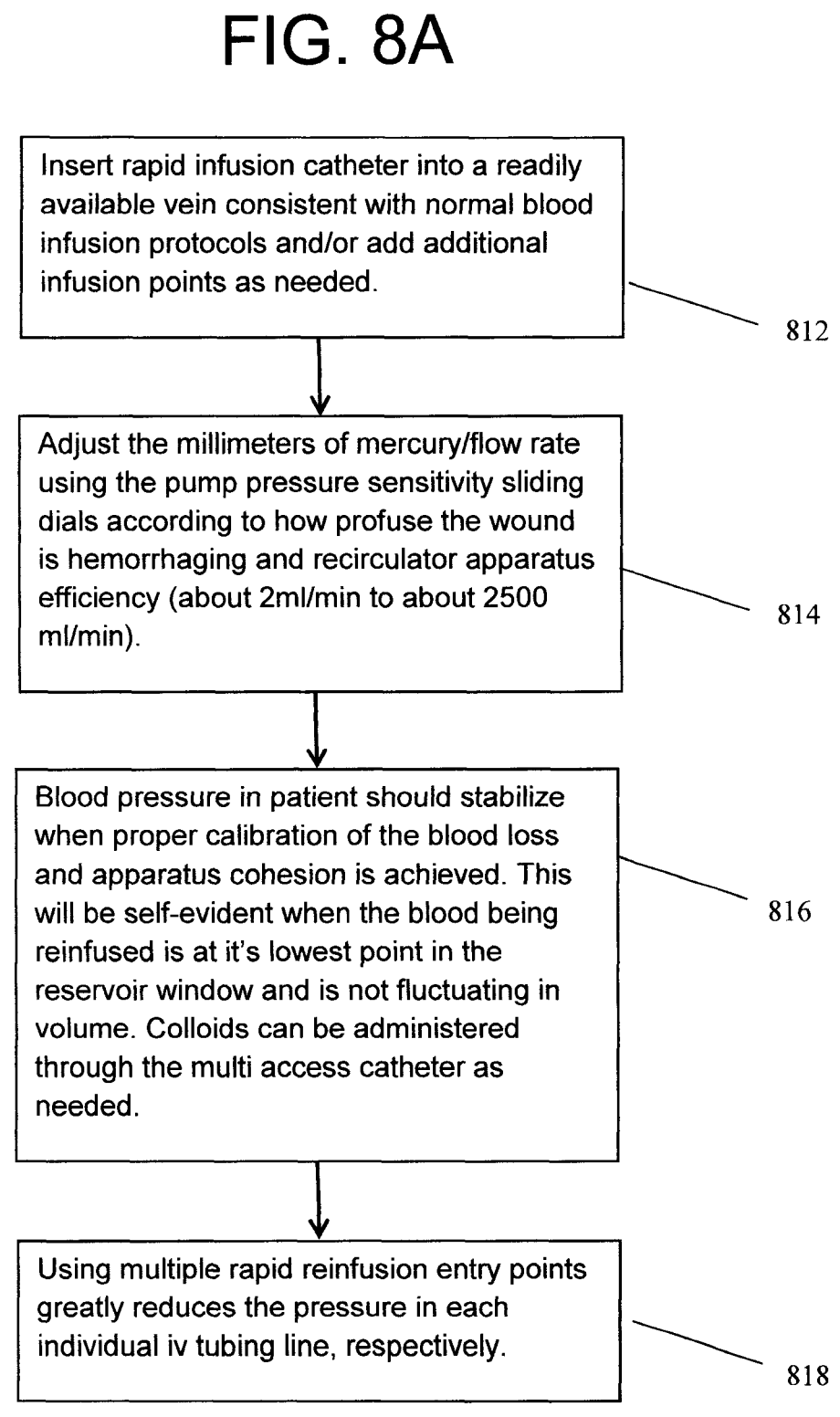

FIG. 8 and FIG. 8*a* is a flow diagram of operating the wound treating apparatus of the disclosure. In step 802, a dose of heparin is administered before or during the procedure. The heparin is administered via the dual port catheter attached to the infusion catheter or iv tubing 106. Next, in step 804, the operator determines which vacuum hose attachment will be suitable for the procedure, based on the diameter of the wound and other determining observations. Step 806 is to turn on vacuum and begin the recirculation procedure, by vacuuming the wounds hemorrhaging blood (internally and/or externally. Next, the infusion pump(s) is turned on in step 808.

Step 810 is after determining the most appropriate site for vascular catheter insertion, let iv tubing prime with blood to the tip of multi access catheter insertion attachment to expel the air, then insert a small guide wire into the vein or access point of choice. The catheter is then advanced over the guide wire and moved into position. The guide wire is then removed. Next, as is shown in step 812 of FIG. 8*a*, the operator inserts rapid infusion catheter into a readily available vein consistent with normal blood infusion protocols and/or add additional infusion points as needed. In step 814 the operator adjusts the millimeters of mercury/flow rate using the pump pressure sensitivity sliding dials according to how profuse the wound is hemorrhaging and recirculator apparatus efficiency (about 2 ml/min to about 2500 ml/min). In step 816 the blood pressure in patient should stabilize when proper calibration of the blood loss and apparatus cohesion is achieved. This will be self-evident when the blood being reinfused is at its lowest point in the reservoir window and is not fluctuating in volume. Colloids can be administered through the multi access catheter as needed. In step 818, using multiple rapid reinfusion entry points greatly reduces the pressure in each individual iv tubing line, respectively.

In a typical non-restrictive embodiment, the vacuum pump and the infusion pump(s) are integrated by being at opposite ends of the unit to recirculate hemorrhaging blood back into the body to maintain blood pressure after serious injuries. The adjustable flow rate rapid infusion pumps have a flow rate of about 2 ml/min to about 2500 ml/min. The replaceable heated filter may be about 200 to about 300 micron aluminum mesh. The amperage of the unit is 12 amps, and the unit may be powered by 40 volt lithium battery. Alternatively, the unit can use 120 volt AC using a 15 foot long power cord. The 2 vacuum pumps have about 6.5 horsepower. The large bore iv tubing has a diameter of about 4 to about 10 mm, and is usually about 4 to about 6.4 mm and is replaceable. A variety of vacuum hose accessories are available. The blood pressure display on the unit is optional. The thermometer display may be digital and may be an LCD display or an LED display. Insulated, heated iv tubing sleeves are optional. All parts are replaceable and many, e.g., the infusion catheter are for single use only.

In some circumstances the blood would need to be heated before reinfusion, which should be almost instantaneous. Heating the blood in the procedural process could be determined by the technician or administrator, and what particular order to apply during the procedure.

Control of the apparatus and procedure can be according to several modes. One mode is a complete manual mode where the operator manually sets the pump speeds and temperature of the reservoir. In this mode there may be no need to have the blood pressure cuff communicate with the apparatus, and the blood pressure display on the apparatus will be optional. The blood pressure on the cuff will be read by the operator and the parameters of flow manually adjusted accordingly.

Another mode of operation may be semi-automatic. In this mode the temperature in the reservoir will be monitored by a controller (computer) and the current to the heater will be adjusted accordingly. The rate of the infusion pump(s) may also be controlled automatically by a controller in response to the blood pressure. However, due to the nature of hemorrhaging, where conditions may change rapidly, the manual mode may be optimal.

Throughout the specification and the embodiments, the following terms take at least the meanings explicitly associated herein, unless the context clearly dictates otherwise.

Relational terms such as "first" and "second," and the like may be used solely to distinguish one entity or action from another entity or action without necessarily requiring or implying any actual such relationship or order between such entities or actions. The term "or" is intended to mean an inclusive "or" unless specified otherwise or clear from the context to be directed to an exclusive form. Further, the terms "a," "an," and "the" are intended to mean one or more unless specified otherwise or clear from the context to be directed to a singular form. The term "include" and its various forms are intended to mean including but not limited to. References to "one embodiment," "an embodiment," "example embodiment," "various embodiments," and other like terms indicate that the embodiments of the disclosed technology so described may include a particular function, feature, structure, or characteristic, but not every embodiment necessarily includes the particular function, feature, structure, or characteristic. Further, repeated use of the phrase "in one embodiment" does not necessarily refer to the same embodiment, although it may. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. A device or structure that is "configured" in a certain way is configured in at least that way, but may also be configured in ways that are not listed.

What is claimed is:

1. An apparatus to treat a hemorrhaging wound, comprising:

at least one vacuum hose;

at least one IV tubing, catheter, or multi access catheter to return blood to a body;

a reservoir to temporarily contain the blood issuing from the vacuum hose;

an ejectable filter between the vacuum hose and the reservoir;

a temperature regulator to regulate a temperature in the reservoir;

at least one vacuum pump connected to at least one pressure regulator;

3 infusion pumps connected to the IV tubing, the catheter, or the multi access catheter to return blood to the body, each infusion pump having a replaceable heated filter downstream and a separate tubing to return blood to the body.

2. The apparatus of claim 1, wherein there are two vacuum hoses.

3. The apparatus of claim 2, further comprising a vacuum pump switch connected to each vacuum hose.

4. The apparatus of claim 1, further comprising an infusion pump switch connected to each infusion pump.

5. The apparatus of claim 1, wherein there are 3 of the IV tubing, the catheter, or the multi access catheter to return blood to the body, with each of the IV tubing, the catheter, or the multi access catheter being attached to a separate infusion pump of the 3 infusion pumps.

6. The apparatus of claim 1, wherein the reservoir is a transparent plastic reservoir.

7. The apparatus of claim 1, wherein there is a replaceable filter downstream from each vacuum pump.

8. The apparatus of claim 1, wherein there is a replaceable filter downstream from each infusion pump.

9. The apparatus of claim 1, wherein each replaceable filter is an about 200 micron filter.

10. The apparatus of claim 1, wherein the temperature regulator includes a temperature sensor, a heater and a controller.

11. The apparatus of claim 1, wherein a blood pressure cuff is in electronic contact with the apparatus.

12. The apparatus of claim 11, further including a blood pressure display in communication with the blood pressure cuff.

13. The apparatus of claim 1, further comprising a hydrophobic vacuum attachment for treating a chest wound, the hydrophobic vacuum attachment comprising a pillow part attached to a drain part having a vacuum connection point and an air vent.

14. The apparatus of claim 1, further comprising an adhesive vacuum attachment, the adhesive vacuum attachment comprising a suction head, an adhesive layer on the suction head, a vacuum connection port on the suction head, and an air vent in communication with the vacuum connection port.

15. A procedure for treating a hemorrhaging wound, comprising:

providing an apparatus of claim 1, administering a dose of anticoagulant to the apparatus before or during the procedure;

applying a vacuum to vacuum blood from the hemorrhaging wound;

turning on at least one of the infusion pumps;

filling the IV tubing to a tip of an insertion attachment;

expelling blood to clear the IV tubing of any trapped air; and inserting the IV tubing via a rapid infusion catheter into a vein consistent with blood infusion protocols; and adjusting millimeters of mercury/flow rate using pump pressure sensitivity sliding dials according to how profuse the hemorrhaging wound is hemorrhaging and apparatus efficiency.

16. The procedure of claim 15, further comprising adding additional infusion points.

17. The procedure of claim 15, further comprising adjusting the flow rate in accordance with how much the wound is bleeding.

18. The procedure of claim 17, wherein the flow rate is from about 2 ml/min to about 2500 ml/min.

19. The procedure of claim 15, wherein there are 2 vacuum pumps and 3 infusion pumps.

* * * * *